United States Patent
Boroczky et al.

(10) Patent No.: US 10,909,674 B2
(45) Date of Patent: Feb. 2, 2021

(54) SYSTEM AND METHOD FOR CONTEXT-AWARE IMAGING

(71) Applicant: KONINKLIJKE PHILIPS N.V., Eindhoven (NL)

(72) Inventors: Lilla Boroczky, Mount Kisco, NY (US); Shyam Bharat, Arlington, MA (US); Bruce Reiner, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 116 days.

(21) Appl. No.: 15/021,974

(22) PCT Filed: Sep. 24, 2014

(86) PCT No.: PCT/IB2014/064792
§ 371 (c)(1),
(2) Date: Mar. 15, 2016

(87) PCT Pub. No.: WO2015/044872
PCT Pub. Date: Apr. 2, 2015

(65) Prior Publication Data
US 2016/0225147 A1 Aug. 4, 2016

Related U.S. Application Data

(60) Provisional application No. 61/883,445, filed on Sep. 27, 2013.

(51) Int. Cl.
*A61B 6/00* (2006.01)
*G06T 7/00* (2017.01)
(Continued)

(52) U.S. Cl.
CPC .......... *G06T 7/0012* (2013.01); *A61B 5/0037* (2013.01); *A61B 5/055* (2013.01);
(Continued)

(58) Field of Classification Search
CPC ............ G06T 2211/424; G06T 7/0012; G06T 2207/30168; G06T 2207/10081;
(Continued)

(56) References Cited

U.S. PATENT DOCUMENTS 5,694,484 A * 12/1997 Cottrell ................... G06T 5/002
382/167
7,532,942 B2 * 5/2009 Reiner ................... G06F 19/321
250/252.1
(Continued)

OTHER PUBLICATIONS

Patton et al., A Genetic Algorithm for Learning Significant Phrase Patterns in Radiology Reports, Jul. 8-12, 2009 [retrieved Sep. 24, 2019], Proceedings 11th Conference Companion on Genetic and Evolutionary Computation Conference, pp. 2665-2670. Retrieved: https://dl.acm.org/citation.cfm?id=1570380 (Year: 2009).*

(Continued)

*Primary Examiner* — Andrew M Moyer
*Assistant Examiner* — Dennis Rosario

(57) ABSTRACT

A method generates images based on context-aware imaging. The method includes acquiring a first image of a patient using first image acquisition parameters. The method includes determining, within the first image, an area as a function of first data associated with the patient. The method includes determining modification data as a function of at least one of (a) second data corresponding to the determined area and (b) the first data. The method includes determining second image acquisition parameters as a function of the modification data and the first image acquisition parameters. The method includes acquiring a second image of the patient using the second image acquisition parameters.

10 Claims, 5 Drawing Sheets

(51) Int. Cl.
  *A61B 5/055* (2006.01)
  *A61B 6/03* (2006.01)
  *A61B 5/00* (2006.01)
  *G01R 33/54* (2006.01)
(52) U.S. Cl.
  CPC .......... *A61B 5/7221* (2013.01); *A61B 6/032* (2013.01); *A61B 6/488* (2013.01); *A61B 6/50* (2013.01); *A61B 6/5294* (2013.01); *A61B 6/545* (2013.01); *A61B 6/037* (2013.01); *A61B 6/5258* (2013.01); *G01R 33/543* (2013.01); *G06T 2207/10088* (2013.01); *G06T 2207/30004* (2013.01); *G06T 2207/30168* (2013.01)
(58) Field of Classification Search
  CPC ............ G06T 7/11; G06T 2207/30004; G06T 2207/10072; G06T 2207/10088; G06T 2210/41; G06T 2207/30016; G06T 2207/10116; G06T 2207/30096; G06T 11/003; G06T 2207/10104; G06T 11/008; G06T 11/005; G06T 7/12; G06T 7/10; G06T 7/97; G06T 2207/10076; G06T 2207/10084; G06T 2207/20128; G06T 2207/20152; G06T 2207/10101; G06T 2207/10108; A61B 5/7221; A61B 5/055; A61B 6/032; A61B 6/504; A61B 6/037; A61B 6/542; A61B 8/4416; A61B 6/468; A61B 6/545; A61B 8/468; A61B 6/5235; A61B 6/025; A61B 6/488; A61B 8/483; G06Q 50/24; G06Q 50/22; G06F 19/00; G06F 19/321; G06F 16/583; G06F 16/58; G06F 16/5866; G06F 17/241; G06F 40/169; G06F 40/30; G06F 40/279; G06F 40/247; G06F 40/56; G16H 50/20; G16H 10/60; G16H 40/20; G16H 15/00; G16H 50/70; G16H 50/30; G16H 30/20; G16H 40/63; G16H 40/40; G16H 40/60; G16H 30/00; G16H 10/00; G06K 2209/05; G06K 2209/01; G06N 20/00; H04L 67/12
  See application file for complete search history.

(56) References Cited

U.S. PATENT DOCUMENTS

| | | | |
|---|---|---|---|
| 7,831,445 B2 | 11/2010 | Reiner | |
| 7,930,193 B2 | 4/2011 | Marx | |
| 8,333,508 B2* | 12/2012 | Reiner | A61B 6/581 378/207 |
| 8,538,776 B2 | 9/2013 | Reiner | |
| 9,600,882 B2* | 3/2017 | Mankovich | G06T 7/0014 |
| 9,646,393 B2* | 5/2017 | Prevrhal | G06T 11/008 |
| 2009/0006131 A1* | 1/2009 | Unger | G16H 50/20 705/3 |
| 2009/0238329 A1 | 9/2009 | Haras | |
| 2009/0279672 A1* | 11/2009 | Reiner | A61B 6/581 378/207 |
| 2009/0290773 A1* | 11/2009 | Holt | G06F 19/321 382/131 |
| 2010/0121178 A1* | 5/2010 | Krishnan | G06F 19/321 600/411 |
| 2010/0145720 A1* | 6/2010 | Reiner | G06Q 50/205 705/2 |
| 2011/0270623 A1* | 11/2011 | Reiner | G06F 19/321 705/2 |
| 2012/0220855 A1 | 8/2012 | Zhang et al. | |
| 2012/0221347 A1* | 8/2012 | Reiner | G06Q 10/00 705/2 |
| 2013/0105699 A1 | 5/2013 | Asma et al. | |
| 2013/0129165 A1 | 5/2013 | Dekel et al. | |
| 2014/0198964 A1 | 7/2014 | Vonberg et al. | |

OTHER PUBLICATIONS

Reinner, Uncovering and Improving Upon the Inherent Deficiencies of Radiology Reporting through Data Mining, Feb. 17, 2010 [ retrieved Feb. 8, 2020], Journal of Digital Imaging, vol. 23, No. 2, pp. 109-118. Retrieved: https://link.springer.com/article/10.1007/s10278-010-9279-4 (Year: 2010).*

Tilkemeier et al., Standardized reporting of radionuclide myocardial perfusion and function, 2009 [retrieved Feb. 8, 2020], Journal of Nuclear Cardiology, 27 pages. Retrieved: https://www.asnc.org/files/Radionuclide%20MP%20&%20Function.pdf (Year: 2009).*

Reiner, New Strategies for Medical Data Mining, Part 3: Automated Workflow Analysis and Optimization, Feb. 2011 [retrieved Aug. 18, 2020], Journal of the American College of Radiology, vol. 8, Issue 2,pp. 132-138. https://doi.org/10.1016/j.jacr.2010.07.004 (Year: 2011).*

Reiner, Quantifying Radiation Safety and Quality in Medical Imaging, Part 2: The Radiation Scorecard, Sep. 2009 [retrieved Aug. 18, 2020], Journal of the American College of Radiology, vol. 6, Issue 9, pp. 615-619. https://doi.org/10.1016/j.jacr.2009.05.008 (Year: 2009).*

Reiner, Automating Radiologist Workflow Part 1: The Digital Consultation, Oct. 2008 [retrieved Aug. 18, 2020], Journal of the American College of Radiology, vol. 5, Issue 10,pp. 1080-1085. https://doi.org/10.1016/j.jacr.2008.05.014 (Year: 2008).*

* cited by examiner

SYSTEM AND METHOD FOR
CONTEXT-AWARE IMAGING

CROSS-REFERENCE TO PRIOR APPLICATIONS

This application is the U.S. National Phase application under 35 U.S.C. § 371 of International Application No. PCT/IB2014/064792, filed on Sep. 24, 2014, which claims the benefit of U.S. Provisional Application No. 61/883,445, filed on Sep. 27, 2013. These applications are hereby incorporated by reference herein.

There is variability among physicians and healthcare institutions in many threads of a medical workflow, such as, for example, variability in (a) quality of physician order entries (e.g., content, level of detail, terminology etc.); (b) image acquisition (e.g. imaging protocols); and (c) radiologist's interpretations and reporting. Therefore, a comprehensive and intelligent quality assurance (QA) system to quantify the above variations and to link physician interpretations to final diagnosis (e.g., pathology correlation) would be beneficial.

The extension of a QA system including context-awareness of the clinical questions that a particular imaging study is meant to answer would be extremely beneficial. Such a tool could help with, for example: identifying components of current radiological workflows that can benefit from improved efficiency; enabling pay-for-performance reimbursements; streamlining QA certification/accreditation/audits; and reducing variation among physicians and institutions. Examples of some reductions in the variations may include: closing the gap between novices and experts; reducing care differences among institutions; enabling the development of objective benchmarks; and improving radiological imaging protocols. The improvement in the radiological imaging protocols may include, for example: discovering hidden correlations between imaging protocols and accuracy of diagnoses; enabling evidence-based modification of imaging protocols; enabling dissemination of best practices; and helping to reduce repeated imaging studies and improve radiology workflow.

Presently, there are few radiology QA systems and the systems that do exist either do not use or merely embed with limitations the awareness of the context of clinical questions into their QA solutions. In addition, these QA systems are not adaptive to patient's specific conditions often hindering quality of the applied process.

A system and method generates images based on context-aware imaging. The method (300) comprises acquiring (305) a first image (200) of a patient using first image acquisition parameters; determining (310), within the first image (200), an area (202) as a function of first data associated with the patient; determining (315) modification data as a function of at least one of (a) second data corresponding to the determined area (202) and (b) the first data; determining (320) second image acquisition parameters as a function of the modification data and the first image acquisition parameters; and acquiring (325) a second image (204) of the patient using the second image acquisition parameters.

Figure 3:
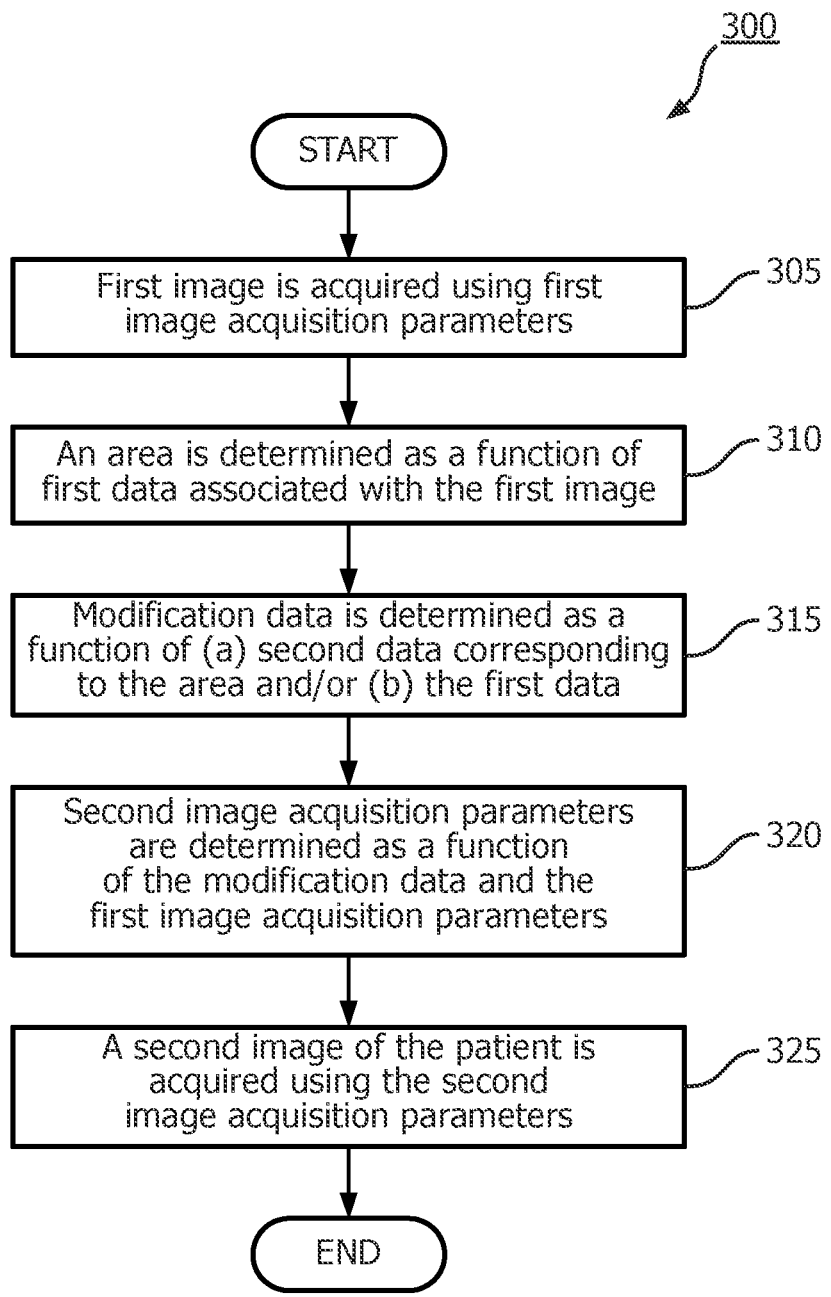

FIG. 3. shows a method according to an exemplary embodiment of the present invention.

Figure 4:
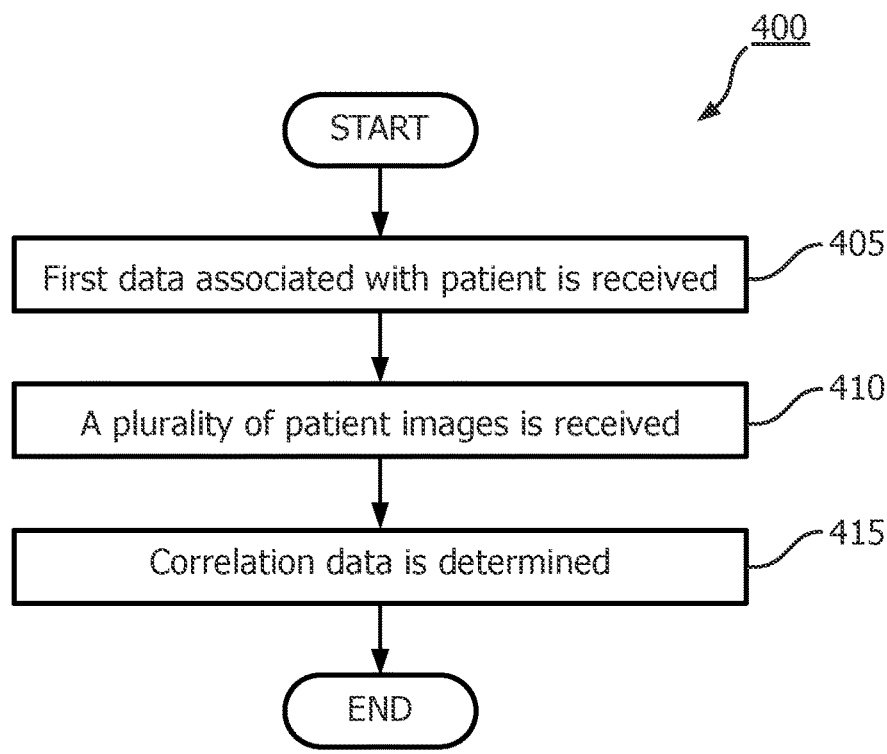

FIG. 4 shows a method according to a further exemplary embodiment of the present invention.

Figure 5:
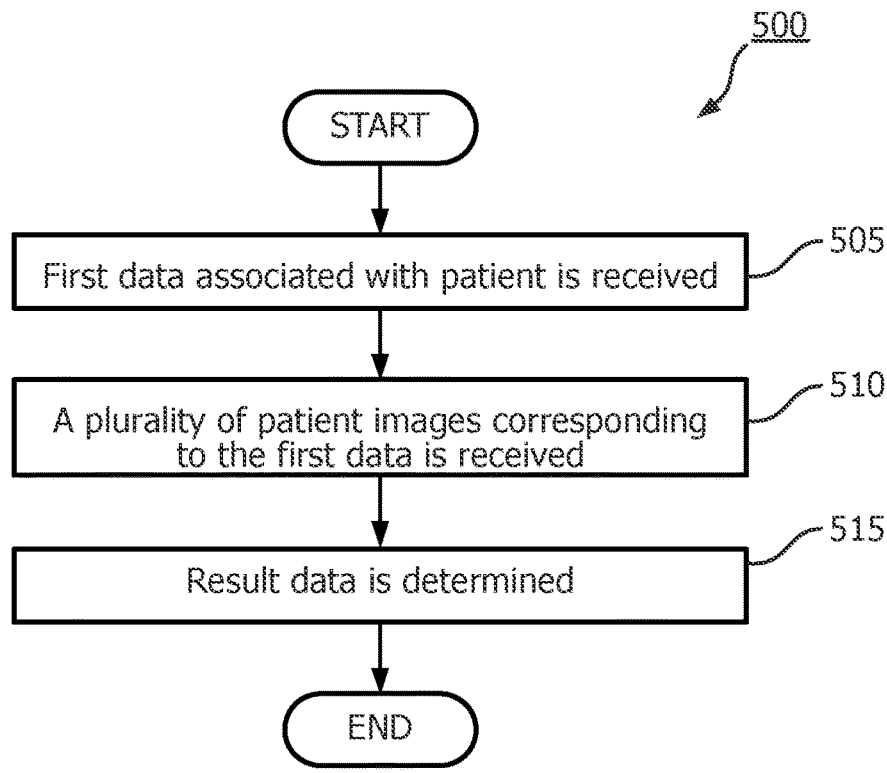

FIG. 5 shows a method according to another further exemplary embodiment of the present invention.

The exemplary embodiments may be further understood with reference to the following description and the appended drawings, wherein like elements are referred to with the same reference numerals. The exemplary embodiments relate to a method and system for utilizing context awareness quality assurance to analyze images. Although the exemplary embodiments are specifically described in regard to a radiology department, it will be understood by those of skill in the art that the system and method of the present invention may be used for patients having any of a variety of diseases or conditions within any of a variety of hospital departments.

Figure 1:
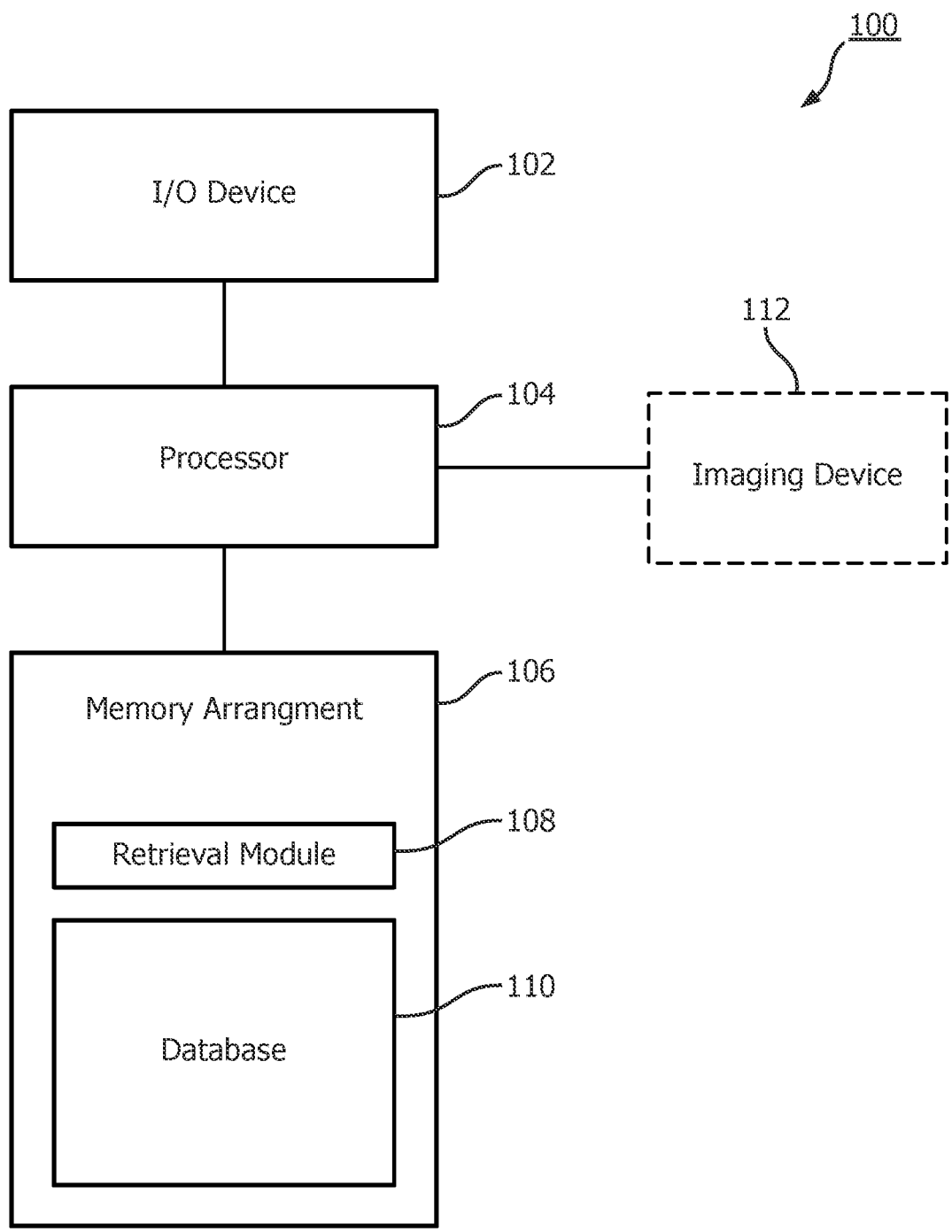
FIG. 1 shows a schematic drawing of a system according to an exemplary embodiment of the present invention.
Figure 2A:
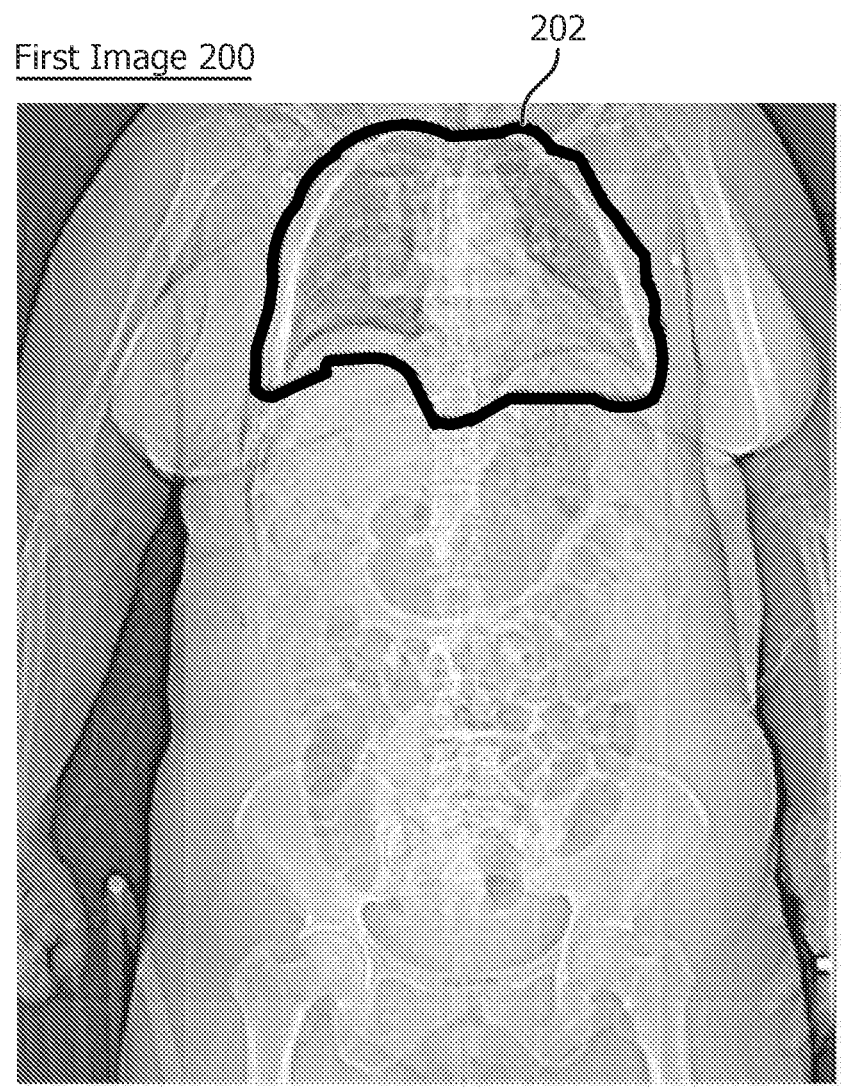
FIG. 2A shows a first image produced utilizing a method according to an exemplary embodiment of the present invention.

FIG. 1 shows a system 100 according to an exemplary embodiment of the present invention. As will be explained below, the system 100 utilizes first data to determine and/or obtain an area in a first image 200 (e.g., a scout image) of a patient, which is shown in FIG. 2A. The system 100 includes an input/output (I/O) device 102, a processor 104, and a memory arrangement 106. The system 100 may be any computing device such as, for example, a computer, a tablet, a handheld device, etc.

The I/O device 102 receives input data from a user via, for example, a mouse, a keyboard, a touch screen, a microphone, an electronic transfer etc. and outputs data to the user via, for example, a display, a speaker, a printer, a predetermined file transfer etc.

The memory arrangement 106 stores data and a plurality of software modules which are executed by the processor 104. For example, the memory arrangement 106 may include a retrieval module 108 configured to retrieve one of a plurality of first images $200_1 \ldots 200_n$ and perform the exemplary method of the present invention; and a database 110 configured to store the first images $200_1 \ldots 200_n$. Elements of the system 100 may be connected using conventional wired connections (e.g., CAT5, USB, etc.), wireless connections (e.g., Bluetooth, 802.11 a/b/g/n, etc.), or any combination thereof.

FIG. 2A shows an exemplary embodiment of the first image 200. The first image 200 of the patient is acquired using first image acquisition parameters before any imaging studies are performed. The first image acquisition parameters may include, for example, use of a first imaging protocol (e.g., MRI, X-ray, PET, etc.) with a first field of view. Those of ordinary skill in the art will understand that the first image acquisition parameters may include any adjustable image acquisition parameters.

The processor 104 is configured to identify an area 202 in the first image 200 based on the first data associated with the patient. The first data may include, for example, a physician order entry (POE), a physician referral, and/or prior patient reports. The physician order entry may include an indication of a potential clinical study to be performed on the patient. However, one of ordinary skills in the art will understand that any information relevant to the patient's treatment may be used.

The system 100 may optionally include an imaging device 112 such as, for example, an MRI, a CT imaging device, an X-ray machine, etc. The imaging device 112 may be used to acquire the first image 200. However, as will be described below with reference to FIGS. 4 and 5, the system 100 is not limited to analyzing the first image 200 acquired by the imaging device 112 and may instead utilize the first images $200_1 \ldots 200_n$ obtained by other devices.

FIG. 3 illustrates an exemplary method of the present invention for determining an area 202 in the first image 200. In step 305, the first image 200 is acquired using the first image acquisition parameters. It should be noted that the first image 200 may be acquired using the imaging device 112 or may be acquired by any device and, e.g., stored in the database 110. In addition, the first image 200 may instead be manually supplied to the processor 104 by a technician.

In step 310, the processor 104 determines the area 202 in the first image 200 based on first data received by the system 100. After receiving the first data, the processor 104 may segment major organs displayed in the first image 200 and determine the area 202 based on the first data. In the example shown in FIG. 2A, the area 202 in the first image 200 is a lung, which may be determined based on the POE.

In step 315, the processor 104 determines modification data based on second data associated with the area 202 and/or the first data. The second data may include, for example, a signal-to-noise ratio, spatial resolution data, and contrast resolution data within the area 202. It should be noted, however, that the second data may include any image characteristics relating to the area 202.

In step 320, the processor 104 determines second image acquisition parameters as a function of the modification data and the first image acquisition parameters. The second image acquisition parameters include adjustments to the first image acquisition parameters and/or new parameters. For example, if the first image 200 was acquired using the first imaging protocol including the first image acquisition parameters, adjustments may be made using these image acquisition parameters to obtain the second image acquisition parameters. Furthermore, the second image acquisition parameters may be from the use of a second imaging protocol that is different than the first imaging protocol. In a further embodiment, certain quality assurance requirements may be relaxed based on the first data. For example, if the patient has emphysema, the time requirement for breath holding may be relaxed. This functionality may be realized in the form of an alert to the imaging technician.

Figure 2B:
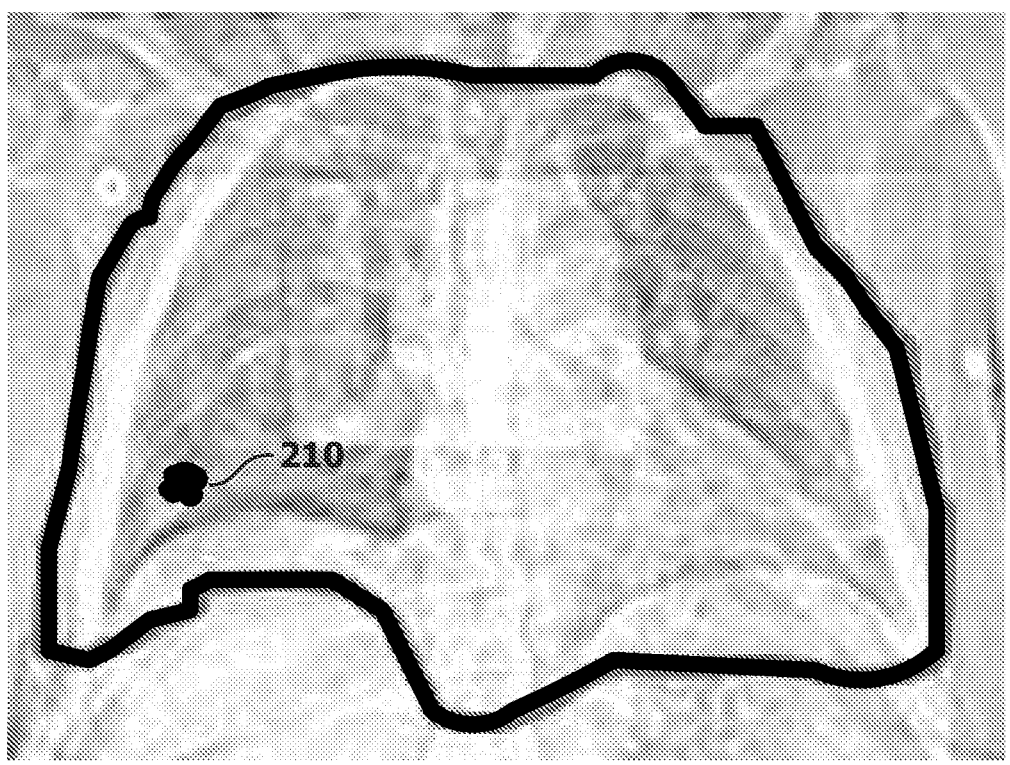
FIG. 2B shows a second image produced utilizing a method according to an exemplary embodiment of the present invention.

In step 325, a second imaging study such as the second image 204 of the patient is acquired using the second image acquisition parameters determined in step 320 (See FIG. 2B). The second image 204 may include a plurality of images or an entire imaging study. The second image 204 may be acquired using, for example, the imaging device 112 of the exemplary system 100. The second image 204 may provide a more detailed view of the area 202 to sufficiently conduct a clinical study. In above-described example of the lung study, the second image 204 may show a nodule 210 in the area 202 that was not originally visible in the first image 200. In a further embodiment, an alert may be provided to the technician if the image quality of the second image 204 falls below a predetermined threshold. For example, there may be a predetermined acceptable number of inadequate image parameters before the image itself is deemed inadequate. The image quality may be determined using some quantifiable measures of image quality, for example, a SNR calculation, resolution data, CNR, etc. In this manner, the image quality metrics may be calculated in real-time during an image acquisition and compared to the predetermined threshold levels. The second image acquisition parameters may be modified in real-time when the quality parameters are below the predetermined threshold. If the threshold is not met, then the acquisition may be stopped, the protocol may be modified, and the imaging may be performed again.

The predetermined set of parameters may be determined based on a retrospective analysis of previous imaging studies. The predetermined set of parameters may include thresholds for the image parameters below which the first image is deemed insufficient to solve a clinical problem. So, for example, the spatial resolution one of the first images retrieved in step 405 is compared with a predetermined spatial resolution threshold. If the spatial resolution of the image is below the threshold, then the image may be deemed inadequate.

FIG. 4 shows a method 400 according to a second exemplary embodiment of the present invention. In step 405, first data associated with the patient is received by the system 100. This first data may substantially correspond to the first data used in the method 300 and may include any information relevant to the patient's treatment. For example, the first data may include the POE, a physician referral, and/or prior patient medical reports.

In step 410, the processor 104 using, for example, the retrieval module 108, retrieves the plurality of first images $200_1 \ldots 200_n$ associated with the patient from the database 110. It should be noted, however, that the first images $200_1 \ldots 200_n$ may instead be manually supplied to the processor 104 by the technician or may be retrieved from a plurality of remotely located databases (not shown). One of ordinary skills in the art will understand that the plurality of first images may be acquired using the same or a plurality of imaging protocols.

In step 415, the processor 104 determines correlation data as a function of the first data and at least one of the image quality data, the plurality of imaging protocols, the image acquisition data, and imaging technician performance data. The correlation may be indicative of patterns between the image quality and the plurality of imaging protocols, the image acquisition data, and imaging technician performance data. To determine the correlation data, the processor 104 may use algorithms to quantify the image quality and relate this information to the imaging protocol, the first image acquisition parameters, and the imaging technician performance data metrics. The determination in step 415 may be performed at different granularities such as, for example, the POE, imaging protocols, stratification of patients, organ sites, operating personnel, etc. For example, the correlation data may include a determination that a certain imaging technician obtains satisfactory brain images but unsatisfactory abdominal scans (i.e., imaging technician performance data).

FIG. 5 shows a method 500 according to a third exemplary embodiment of the present invention. Step 505 is substantially the same as step 405 of method 400 (See FIG. 4). However, instead of retrieving all of the first images associated with the patient (e.g., as in step 410), the first images associated with the first data received in step 505 are retrieved in step 510. The first images received in step 510 include image parameters, which may include, for example, signal-to-noise ratio, contrast, spatial resolution, etc.

In step 515, the processor 104 determines result data as a function of the image parameters of the first images retrieved in step 510 and a predetermined set of parameters. The result data may provide a link for quantified image quality metrics or objective assessment of image quality to correspond to subjective assessments of the image quality. The subjective assessment of the image quality may be based upon an image quality rating provided by a radiologist, technologist, operator, etc. For example, the subjective assessment of the image quality may be "excellent," "good," "average," "bad," etc. The subjective assessment of the image quality may be used as a basis of determining whether an image is deemed inadequate. For example, if the radiologist determines that the image quality is "excellent," the image quality metrics may be deemed to produce adequate images. In another example, if the radiologist determines that the image quality is "bad," then the image quality metrics may be deemed to produce inadequate images. When the radiologist determination and/or the objective image quality metrics indicate inadequate images, the image acquisition parameters may be updated.

Accordingly, the objective image quality metrics of the images may be automatically determined.

It is noted that the claims may include reference signs/numerals in accordance with PCT Rule 6.2(b). However, the present claims should not be considered to be limited to the exemplary embodiments corresponding to the reference signs/numerals.

Those skilled in the art will understand that the above-described exemplary embodiments may be implemented in any number of manners, including, as a separate software module, as a combination of hardware and software, etc. For example, the retrieval module 108 may be a program containing lines of code that, when compiled, may be executed by processor 104 to perform the exemplary method 300.

It will be apparent to those skilled in the art that various modifications may be made to the disclosed exemplary embodiments and methods and alternatives without departing from the spirit or scope of the disclosure. Thus, it is intended that the present invention cover the modifications and variations provided that they come within the scope of the appended claims and their equivalents.

What is claimed is:

1. A method, comprising:
    acquiring a first image of a patient using first image acquisition parameters;
    acquiring first data associated with the patient, wherein the acquired first data is at least one of a physician order entry, a physician referral or medical reports of the patient;
    segmenting, by a processor, an area within the acquired first image based on the acquired first data;
    utilizing, by the processor, a context word in the acquired first data wherein one of the used first image acquisition parameters is determined based on the utilized context word;
    determining, by the processor, second data based on image characteristics within the segmented area;
    determining, by the processor, second image acquisition parameters as a function of the determined second data and the used and determined first image acquisition parameters;
    acquiring, from one of an MRI, a tomographic imaging device or an X-ray machine, a second image of the patient using the determined second image acquisition parameters;
    receiving an indication that the acquired second image is inadequate;
    determining objective image quality metrics of the acquired second image; and
    updating the determined and used second image acquisition parameters as a function of the objective image quality metrics and the utilized context word to receive an indication that the acquired second image is adequate.

2. The method of claim 1, wherein the physician order entry includes an indication of a potential clinical study to be performed on the patient.

3. The method of claim 1, wherein the first data includes information acquired from a plurality of patient medical reports.

4. The method of claim 1, wherein determining the second image acquisition parameters includes the substep of selecting an imaging protocol.

5. The method of claim 4, further comprising:
    adjusting, based on the first data, quality assurance requirements of the selected imaging protocol.

6. The method of claim 1, further comprising:
    alerting a user if the objective quality metrics of the second image are below a predetermined threshold.

7. The method of claim 6, wherein the second image acquisition parameters are modified in real-time when the objective quality metrics are below the predetermined threshold.

8. The method of claim 6, wherein the predetermined threshold is determined as a function of previously performed imaging studies.

9. The method of claim 1, wherein the second data comprises at least one of a signal-to-noise ratio, spatial resolution data and contrast resolution data.

10. A system, comprising:
    a memory arrangement storing a retrieval module, the retrieval module being configured to retrieve a plurality of first images associated with a patient;
    a processor configured to (i) retrieve a first image of the patient, the first image acquired using first image acquisition parameters, (ii) acquire first data associated with the patient, wherein the acquired first data is at least one of a physician order entry, a physician referral and medical reports of the patient; (iii) segment, by a processor, an area within the acquired first image based on the first data (iv) utilize, by the processor, a context word in the acquired first data wherein one of the used first image acquisition parameters is determined based on the utilized context word; (v) determine second data based on image characteristics within the segmented area; and (vi) determine second image acquisition parameters as a function of the determined second data and the used and determined first image acquisition parameters; and
    a medical imaging device consisting of one of an MRI, a tomographic imaging device or an X-ray machine configured to acquire a second image of the patient using the determined second image acquisition parameters, wherein
    the processor is further configured to receive an indication that the acquired second image is inadequate; determine objective image quality metrics of the acquired second image; and update the determined and used second image acquisition parameters as a function of the objective image quality metrics and the context word to receive an indication that the acquired second image is adequate.

* * * * *